US00PP18372P2

(12) United States Plant Patent
Olsthoorn

(10) Patent No.: US PP18,372 P2
(45) Date of Patent: Dec. 25, 2007

(54) *SPATHIPHYLLUM* PLANT NAMED 'SWEET ROBERTA'

(50) Latin Name: *Spathiphyllum Schott*
Varietal Denomination: Sweet Roberta

(75) Inventor: Petrus C. M. Olsthoorn, Honselersdijk (NL)

(73) Assignee: P. C. M. Olsthoorn Holding BV, Honselersdijk (NL)

( * ) Notice: Subject to any disclaimer, the term of this patent is extended or adjusted under 35 U.S.C. 154(b) by 0 days.

(21) Appl. No.: 11/442,937

(22) Filed: May 30, 2006

(51) Int. Cl.
*A01H 5/00* (2006.01)

(52) U.S. Cl. ..... Plt./364

(58) Field of Classification Search ..... Plt./364
See application file for complete search history.

*Primary Examiner*—Kent Bell
*Assistant Examiner*—Annette Para

(57) ABSTRACT

A new cultivar of *Spathiphyllum* plant named 'Sweet Roberta' that is characterized by white spathes, green leaves and a large overall size.

1 Drawing Sheet

Botanical classification: *Spathiphyllum Schott.*
Variety denomination: 'Sweet Roberta'.

BACKGROUND OF THE INVENTION

The present invention relates to a new and distinct cultivar of *Spathiphyllum* plant botanically known as *Spathiphyllum Schott.* and hereinafter referred to by the cultivar name 'Sweet Roberta'.

'Sweet Roberta' is a hybrid that originated from the hybridization of the female or seed parent a proprietary *Spathiphyllum Schott.* identified as 96338-63 (not patented) and the male or pollen parent a proprietary *Spathiphyllum Schott.* identified as 96361-5 (not patented). The cultivar 'Sweet Roberta' was selected by the inventor in September of 1999 as a single plant within the progeny of the stated cross in Honselersdijk, The Netherlands.

Asexual reproduction by tissue culture of the new cultivar 'Sweet Roberta' was first performed in 2000 in Honselersdjik, The Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new Spathiphyllum cultivar 'Sweet Roberta'.

1. Spathiphyllum 'Sweet Roberta' exhibits white spathes.
2. Spathiphyllum 'Sweet Roberta' exhibits green leaves.
3. Spathiphyllum 'Sweet Roberta' exhibits large overall size.

The closest comparison cultivar is *Spathiphyllum* 'Sweet Lauretta'. The new cultivar 'Sweet Roberta' is distinguishable from 'Sweet Lauretta' by the following characteristics:

1. 'Sweet Roberta' has a larger overall size than 'Sweet Lauretta'.
2. 'Sweet Roberta' has darker green leaves than those of 'Sweet Lauretta'.

The new cultivar 'Sweet Roberta' is distinguishable from the male parent *Spathiphyllum* '96361-5' in having darker leaves. The new cultivar 'Sweet Roberta' is distinguishable from the female parent *Spathiphyllum* '96338-63' in having fewer shoots, lighter green leaves and a larger height.

BRIEF DESCRIPTION OF THE DRAWING

The accompanying photograph illustrates the distinguishing traits of *Spathiphyllum* 'Sweet Roberta'. The plant in the photograph shows an overall view of a 57 week old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Spathiphyllum* cultivar named 'Sweet Roberta'. Data was collected in Honselersdijk, The Netherlands from 57 week old greenhouse grown plants in 2 liter containers. The time of year was Spring and the average temperatures was 22 degrees Centigrade during the day and 20 degrees Centigrade at night. No photoperiodic treatments were used. 80–100 PPM of Gibberallic acid was applied for flower initiation. Color determinations are in accordance with The Royal Horticultural Society Colour Chart 2001 edition, except where general color terms of ordinary dictionary significance are used. The growing requirements are similar to the species. 'Sweet Roberta' has not been tested under all possible conditions and phenotypic differences may be observed with variations in environmental, climatic, and cultural conditions, however, without any variance in genotype.

Botanical classification: *Spathiphyllum Schott.* 'Sweet Roberta'.
Use: Ornamental.
Parentage: 'Sweet Roberta' is a hybrid plant that resulted from the hybridization of the following parent plants:
*Female parent.*—A proprietary *Spathiphyllum Schott.* identified as '96338-63'.
*Male parent.*—A proprietary *Spathiphyllum Schott.* identified as '96361-5'.
Vigor: Moderate.
Growth rate: Moderate.

Growth habit: Moderately branching from base, bushy and dense.
Plant shape: Inverted triangle with inflorescences on top.
Suitable container size: 2 liter container.
Height: Average 72 cm to top of leaf plane, 85 cm to top of inflorescences.
Width: Average 91 cm in width.
Hardiness: USDA Zone 10.
Propagation: Tissue Culture.
Time to initiate roots (summer and winter): Approximately 14 days to produce roots on an initial cutting.
Time to produce a rooted cutting or liner (summer and winter): Approximately 39 days.
Root system: Fine and fibrous.
Stem: No stems only clumps, Average 8 clumps, clump color 141B to 14C.
Foliage:
*Texture.*—Smooth with furrowed veins.
*Appearance.*—Glossy.
*Leaf arrangement.*—Alternate.
*Compound or single.*—Single.
*Leaf shape.*—Elliptic to ovate.
*Leaf apex.*—Long apiculate.
*Leaf base.*—Attenuate.
*Leaf length.*—Average 41.9 cm. in length.
*Leaf width.*—17.8 cm in width.
*Quantity of leaves per clump.*—Average 8.
*Pubescence.*—Absent.
*Leaf margin.*—Entire, slightly wavy.
*Vein pattern.*—Pinnate.
*Young leaf color* (*upper surface*).—141A to 143A.
*Young leaf color* (*lower surface*).—137C.
*Mature leaf color* (*upper surface*).—137A to 139A.
*Mature leaf color* (*lower surface*).—137B.
*Vein color* (*lower surface*).—141B.
*Vein color* (*upper surface*).—144B to 144C.
*Leaf attachment.*—Petiolate.
*Petiole dimensions.*—Average 30.1 cm in length excluding geniculum, 6 mm in diameter below geniculum to 9 mm in diameter above clump.
*Petiole aspect.*—Round.
*Petiole color.*—137B, base 137C.
*Geniculum dimensions.*—Average 4.5 cm in length and 7.0 mm in diameter.
*Geniculum aspect.*—Rounded, glabrous.
*Geniculum color.*—144C.
*Petiole sheath dimensions.*—Average 21.4 cm in length and 8 mm in diameter.
*Petiole sheath color.*—137A to 137B.
*Durability of foliage to stress.*—High.
Inflorescence:
*Inflorescence arrangement.*—Spathes with spadices held in between and above the foliage.
*Flowering habit.*—Continuous.
*Quantity of spathes per plant.*—Average 5.
*Natural flowering season.*—Autumn to spring.
*Time to flower or response time.*—55 weeks.
*Fragrance.*—Strong, sweet, and pleasant.
*Self-cleaning or persistent.*—Persistent.
*Flower longevity.*—Lasts approximately 3 weeks on plant.
*Spathe aspect.*—Slightly cupped.
*Spathe dimensions.*—Average 15.8 cm in length, 5.9 cm in width.
*Spathe texture.*—Glabrous, slightly leathery.
*Spathe shape.*—Elliptical.
*Spathe margin.*—Entire.
*Spathe apex.*—Long apiculate.
*Spathe color when opening* (*front side*).—155C, tip and veins 143B.
*Spathe color when opening* (*back side*).—155C, tip and veins 143B.
*Spathe color when fully opened* (*front side*).—155C, tip and veins 143B.
*Spathe color when fully opened* (*back side*).—155C, tip and veins 143B.
*Spathe color fading to.*—Not fading.
*Spadix shape.*—Columnar, arising from top of peduncle.
*Spadix tip.*—Obtuse.
*Spadix base.*—Obtuse.
*Spadix dimensions.*—Average 4.3 cm in length and 1.4 mm in diameter.
*Spadix color when opening.*—155D to 158D.
*Spadix color when fully opened.*—158D.
*Quantity of flowers per spadix.*—Average 120.
*Spadix flower arrangement.*—Bisexual, rounded.
*Spadix flower dimensions.*—3.5 mm in diameter and 3 mm in depth.
Reproductive organs:
*Anther color.*—155D.
*Amount of pollen.*—Moderate.
*Pollen color.*—155D.
*Stigma color.*—155D.
*Ovary color.*—155D.
Peduncle:
*Peduncle dimensions.*—Average 63.8 cm in length and 6.0 mm. in diameter.
*Peduncle angle.*—15° from vertical.
*Peduncle color.*—137B.
*Peduncle strength.*—Strong.
Seed: Seed production has not been observed.
Disease and insect resistance: Plants of the new *Spathiphyllum* have not been observed for disease or insect resistance.

It is claimed:

1. A new and distinct variety of *Spathiphyllum* plant named 'Sweet Roberta' as described and illustrated.

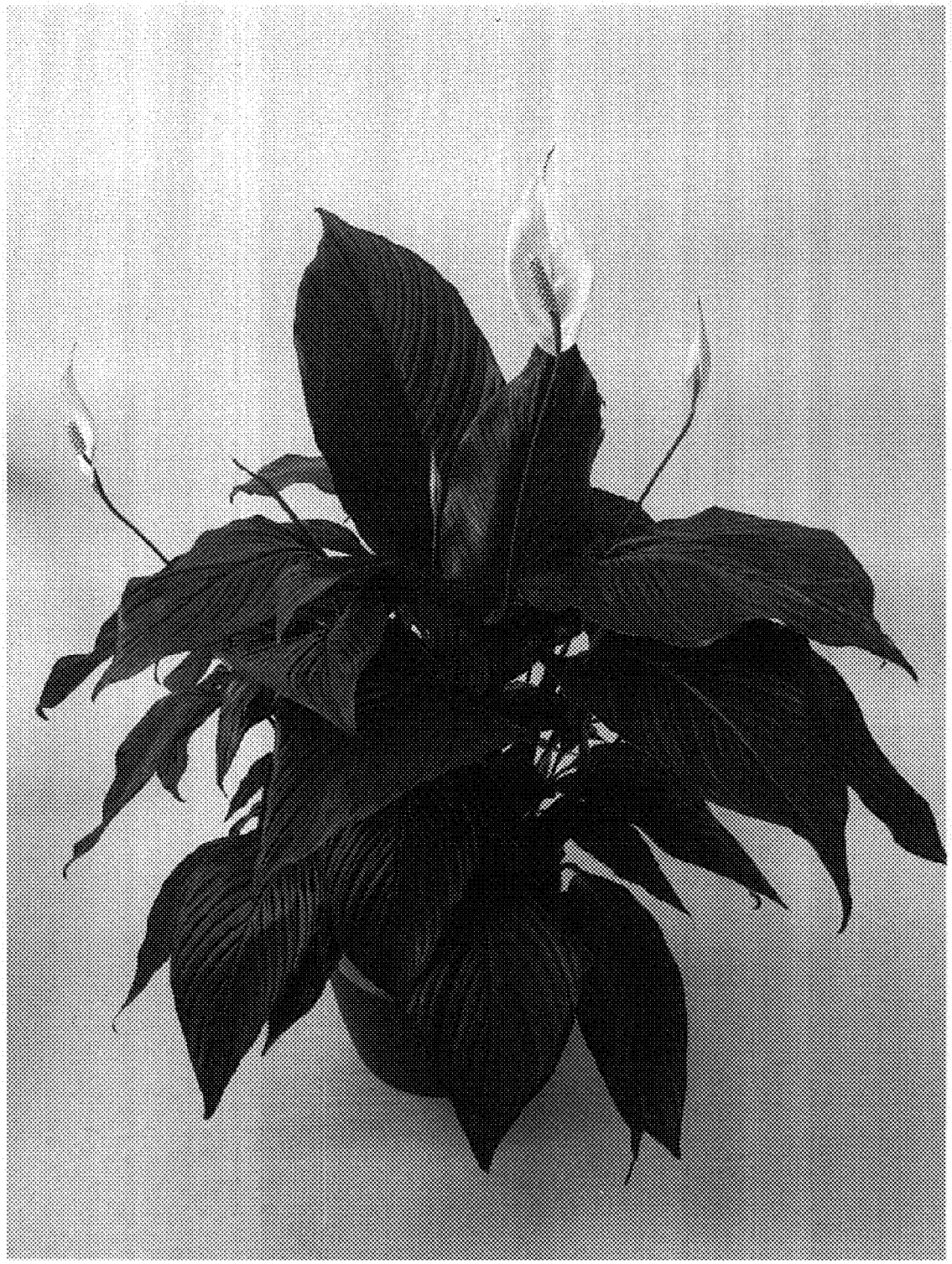

* * * * *